United States Patent [19]
Satoh et al.

[11] Patent Number: 5,416,105
[45] Date of Patent: May 16, 1995

[54] TREATING AN ARTERIOSCLEROSIS WITH GLIMEPIRIDE

[75] Inventors: Yusuke Satoh, Kawagoe; Toshifumi Inami, Abiko, both of Japan

[73] Assignee: Hoechst Japan Limited, Tokyo, Japan

[21] Appl. No.: 172,145

[22] Filed: Dec. 23, 1993

[30] Foreign Application Priority Data

Dec. 28, 1992 [JP] Japan ............... 4-347476

[51] Int. Cl.$^6$ ............... A61K 31/095; A61K 31/40
[52] U.S. Cl. ............... 514/423; 514/824
[58] Field of Search ............... 514/423, 824

[56] References Cited

U.S. PATENT DOCUMENTS

| | | | |
|---|---|---|---|
| 4,379,785 | 4/1983 | Weyer et al. | 424/244 |
| 4,411,903 | 10/1983 | Shepherd | 424/267 |
| 5,082,856 | 1/1992 | Taniguchi et al. | 514/423 |

FOREIGN PATENT DOCUMENTS 0031058  7/1981  European Pat. Off.

OTHER PUBLICATIONS

Y. Ozaki et al., "Effects of Oral Hypoglycaemic Agents on Platelet Functions", Biochemical Pharmacology, vol. 44, No. 4, pp. 687–691, 1992.

M. Omosu et al., "Effects of Hoe 490, A New Oral Antidiabetic Agent, on Platelet Aggregation", Japan J. Pharmacol., vol. 49, p. 328P, 1989.

Z. Aranyi, "Clinical and Experimental Comparison of the Cardiovascular Effects of Glibenclamide, Glimepiride and Gliclazide in Diabetes", vol. 24, Supplement I, p. S228, 1992.

G. Marquié, "Effets Préventifs du Gliclazide sur le Développement de l'athérosclérose induite par le cholestérol chez le Lapin", C. R. Acad. Sc. Paris, Série D, vol. 285, pp. 197–200, Jul. 11, 1977.

*Primary Examiner*—Raymond Henley, III
*Assistant Examiner*—T. J. Criares
*Attorney, Agent, or Firm*—Finnegan, Henderson, Farabow, Garrett & Dunner

[57] ABSTRACT

A pharmaceutical composition containing as an active ingredient glimepiride. The composition is used for preventing or treating arteriosclerosis with no influence on lipid metabolism and no increase in plasma insulin level.

4 Claims, 3 Drawing Sheets

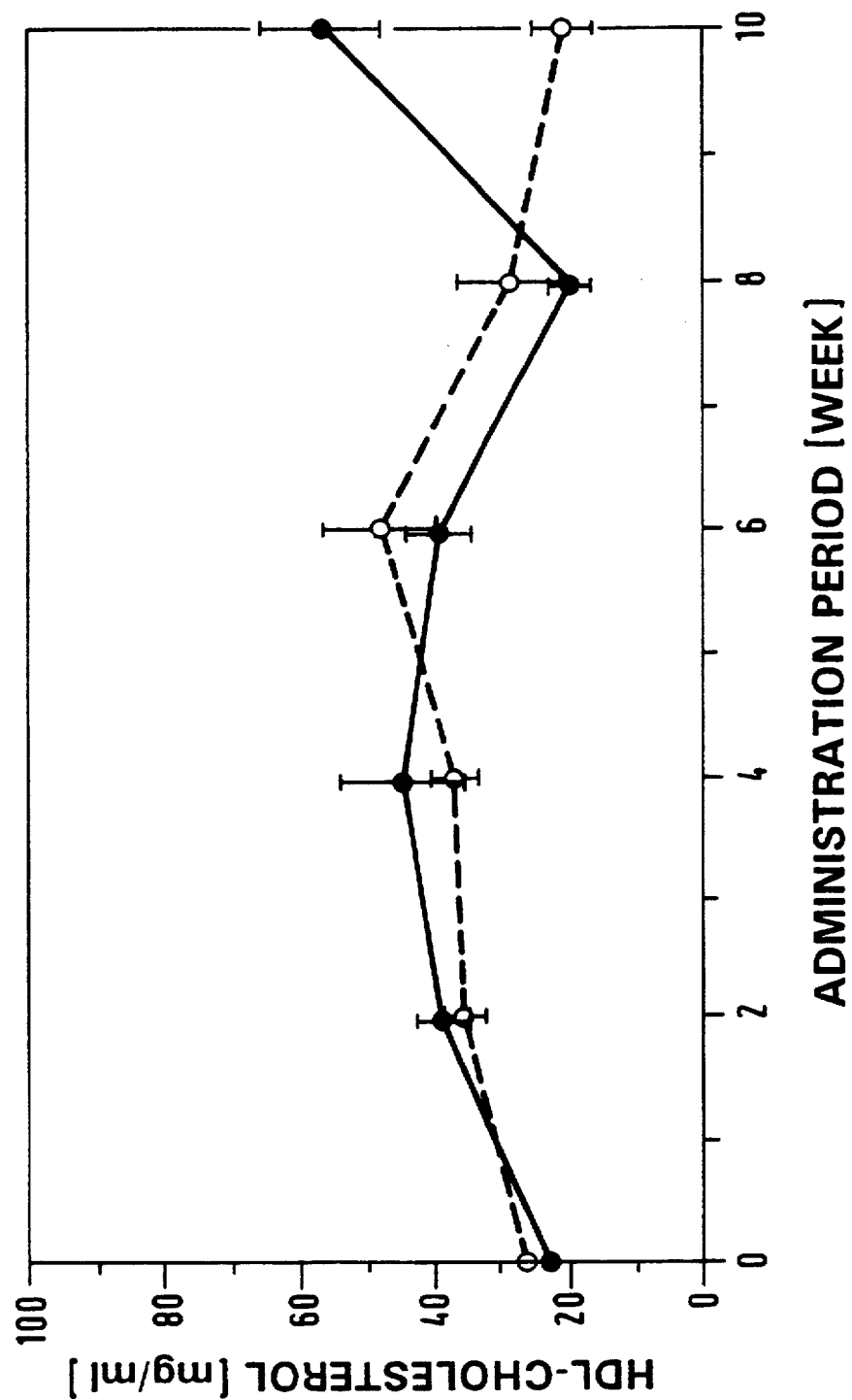

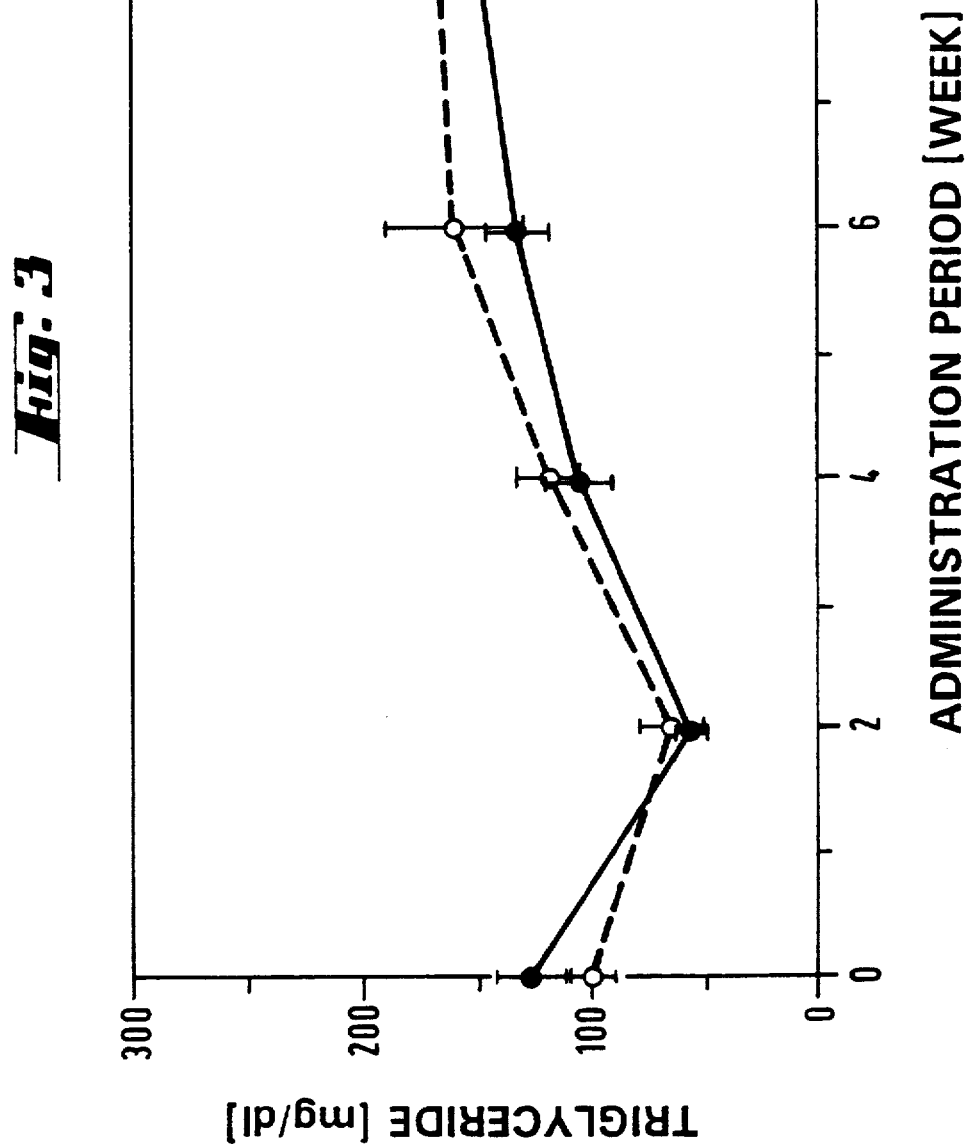

TREATING AN ARTERIOSCLEROSIS WITH GLIMEPIRIDE

This invention relates to a pharmaceutical composition for preventing or treating arteriosclerosis and the use of glimeperide for the preparation of such a composition.

Arteriosclerosis has been considered to be caused by obesity, hypertension, platelet hyperergasia, hyperlipemia, hyperinsulinism and smoking and others. Prior arteriosclerosis-treating agents include lipemia-treating agents such as mevalotin and anti-platelet agents such as aspirin. As mechanism of the action of such agents are mentioned reduction in blood cholesterol due to inhibition of HMG-CoA reductase, a rate-determining enzyme in the cholesterol synthetic route or platelet aggregation inhibition via inhibition of platelet cyclooxygenase. The above-mentioned agents are effective in the treatment of arteriosclerosis, but there has been desired an arteriosclerosis-treating agent which could be more effective or depend upon other mechanism of action. The present invention has the possibility to realize this desire.

This invention is directed to a pharmaceutical composition for preventing or treating arteriosclerosis containing as an active ingredient glimepiride, which is a generic name of 1-[4-[2-(3-ethyl-4-methyl-2-oxo-3-pyrroline-1-carboxyamido)ethyl]-phenylsulfonyl]-3-(trans-4-methylcyclohexyl)-urea represented by the formula (I)

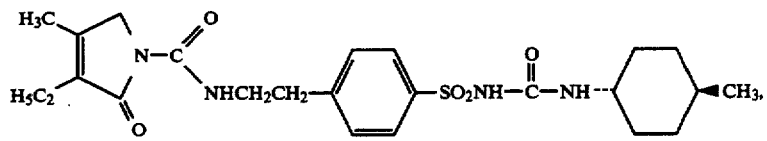

or a physiologically acceptable salt of glimepiride.

The invention is furthermore directed to the use of glimepiride or a physiologically acceptable salt thereof for the preparation of such a composition. The composition comprises the active substance and if desired, pharmaceutically acceptable fillers, carriers and/or excipients.

The present composition is particularly effective in the prevention and treatment of cerebrosclerosis, coronary arteriosclerosis and arteriosclerotic nephrosis. Glimepiride is a sulfonylurea drug (SU drug) described in EP-B-0031058 (U.S. Pat. No. 4,379,785), which is expected to be useful as a hypoglycemic agent in non-insulin-dependent diabetic patients. Assured pharmacological actions of the drug include an action of stimulating the insulin secretion from pancreatic β cells, an action of accelerating the glucose uptake in peripheral tissues and inhibition of cyclooxygenase. The action of stimulating the insulin secretion, however, is milder than those of some other SU drugs. As a result of extensive studies, we have found that glimepiride can inhibit atherogenesis developed in rabbits fed on high cholesterol diet. The present invention has been completed upon such finding.

Glimepiride is administered at a daily dose for adults of 1-32 mg human/day [about 0.01-0.5 mg (in a body weight ratio)/kg/day] for the prevention and treatment of arteriosclerosis.

According to the present invention glimepiride or a physiologically acceptable salt thereof may be administered orally, intravenously, intramuscularly or via other routes, and may be applied in the dosage form of tablets, sugar coated tablets, pills, capsules, powders, granules, suppositories and others. Tablets may be preferable for oral administration. For example, a tablet contains preferably from 0, 1 to 20 mg, in particular from 0,5 to 1 mg, of glimepiride. Glimepiride or a physiologically acceptable salt thereof may be admixed with any pharmaceutically acceptable fillers and formulated into any of the above dosage forms according to a conventional method.

Also, glimepiride has been administered as a hypoglycemic agent to more than 3000 patients at home and abroad. The drug has been administered neither with adverse reaction nor with side effect at said dose of 1-32 mg/human/day. The results of the acute toxicity test are shown in Table 1.

TABLE 1

| Animal species | Administration route | Sex | $LD_{50}$ (mg/kg) |
|---|---|---|---|
| Mice | | | |
| NMRI strain | p.o. | Male | >10000 |
| Male/Female | | Female | >10000 |
| 5 animals/group/each | | | |
| Mice | | | |
| NMRI strain | i.p. | Male | >4000 |
| Male/Female | | Female | >4000 |
| 3 animals/group/each | | | |
| | | | (Slight decrease in spontaneous movement observed at 4000 mg/kg) |
| Rats | | | |
| Wistar strain | p.o. | Male | >10000 |
| Male/Female | | Female | >10000 |
| 5 animals/group/each | | | |
| Rats | | | |
| Wistar strain | i.p. | Male | >3950 |
| Male/Female | | Female | >3950 |
| 3 animals/group/each | | | |
| | | | (Slight decrease in spontaneous movement observed at 3950 mg/kg) |

Example 1

The preventive and therapeutic effect of the present glimepiride on arteriosclerosis will be illustrated by way of the following Examples.

Preventing and curative effects on atherogenesis in rabbits fed on high cholesterol diet Male New Zealand strain white rabbits 10 weeks old were fed on 1% cholesterol diet for 10 weeks to induce hypercholestemia. A group of 8 rabbits was given glimepiride blended in a daily 100 g diet at a dose of 0. 1 mg/kg/day (8 rabbits represented the control group). The dosage was determined on the basis of clinical use in humans. Plasma lipid parameters (total cholesterol, HDL cholesterol and triglyceride) and plasma insulin levels were measured at a predetermined interval. After completion of the administration period, the thoracic aorta was isolated and stained for atherosclerotic lesions deposited on the inner wall of the blood vessel according to an oil red method (Lillie, R. D. (1944), Stain Technology, vol. 19, p. 55). Blood was drawn when the stomach was empty, and plasma was centrifugally separated for the lipid measurement.

The fasting plasma total cholesterol levels in rabbits fed on high cholesterol diet are shown in FIG. 1, the HDL cholesterol levels are in FIG. 2 and the triglyceride levels are in FIG. 3, respectively. The statistical examination (Student test) has revealed no significant difference between the medicated groups and the control groups (the non-medicated groups) in regard to plasma lipids.

The fasting plasma insulin levels in rabbits fed on high cholesterol diet are shown in Table 2, while the area rate (%) of the atherosclerotic lesions deposited on the inner wall of the blood vessel are shown in Table 3.

TABLE 2

| Week<br>Compound | 0 | 2 | 4 | 6 | 8 | 10 |
|---|---|---|---|---|---|---|
| Control group | 12.7 ± 1.7 | 12.9 ± 1.8 | 10.3 ± 1.4 | 12.3 ± 1.4 | 10.8 ± 1.6 | 11.0 ± 1.4 |
| Glimepiride administered group | 12.8 ± 2.3 | 9.1 ± 1.5 | 7.7 ± 1.4 | 7.9 ± 1.5 | 8.8 ± 2.4 | 7.4 ± 1.2 |

TABLE 3

| | Dose (mg/kg) | Area percent of atherosistic lesions (%) |
|---|---|---|
| Control group | — | 57.50 ± 7.13 |
| Glimepiride administered group | 0.1 | 20.61 ± 4.79** |

**Means ± standard error, $P < 0.01$

In FIG. 1, there was no difference in plasma lipids between the control group and the medicated group thereby demonstrating that glimepiride had no influence upon lipid metabolism. Significant effect was not seen by the glimepiride administration in fasting plasma insulin levels in Table 2. As seen in Table 3, area percent of the atherosclerotic lesions was significantly decreased in the glimepiride administered group as compared with the control group. In consideration of the results that there is no difference between the control group and the glimepiride administered group in plasma lipids and plasma insulin in the above test, the arteriosclerosis-inhibiting effect of the glimepiride could not be considered via the serum lipids or insulin which may be one of the dangerous factors for inducing arteriosclerosis, but would be considered to be via any other actions.

The composition of the invention is therefore used for preventing or treating arteriosclerosis with no influence on the lipid metabolism and no significant increase in fasting plasma insulin level.

Example 2 (formulation)

By using 10 g of glimepiride, 700 g of lactose, 40 g of corn starch, 5 g of polyvinyl pyrolidone, 100 g of crystalline cellulose and 5 g of magnesium stearate, tablets, each containing 1 mg of glimepiride, were prepared according to a conventional method.

BRIEF DESCRIPTION OF THE DRAWINGS

FIG. 2 shows a HDL-cholesterol level in blood.
FIG. 3 shows a triglyceride level in blood.
○: Control groups
●: Glimepiride administered groups

Figure 1:
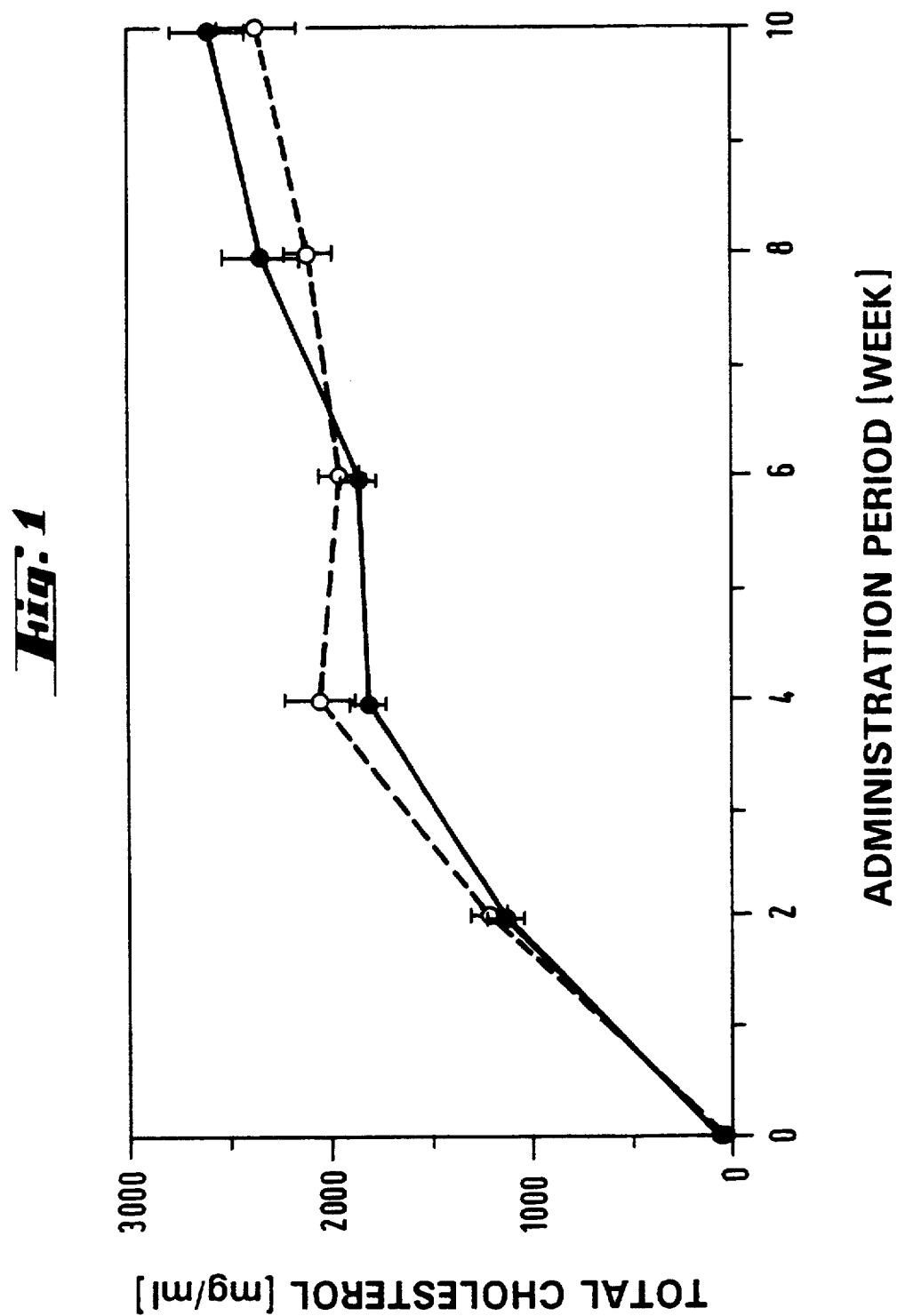
FIG. 1 shows a total cholesterol level in blood.

What is claimed is:

1. A method for preventing or treating arteriosclerosis comprising administering to a subject in need thereof an effective amount of glimepiride or of a physiologically acceptable salt thereof.

2. The method according to claim 1, wherein the arteriosclerosis is a cerebrosclerosis.

3. The method according to claim 1 wherein the arteriosclerosis is a coronary arteriosclerosis.

4. The method according to claim 1 wherein the arteriosclerosis is an arteriosclerotic nephrosis.

* * * * *